United States Patent [19]

Elstner

[11] Patent Number: 4,629,696
[45] Date of Patent: Dec. 16, 1986

[54] PROCESS FOR THE SELECTIVE PRODUCTION OF REDUCED OXYGEN SPECIES

[75] Inventor: Erich Elstner, Grobenzell, Fed. Rep. of Germany

[73] Assignee: Boehringer Mannheim GmbH, Mannheim, Fed. Rep. of Germany

[21] Appl. No.: 537,445

[22] Filed: Sep. 30, 1983

[30] Foreign Application Priority Data

Oct. 1, 1982 [DE] Fed. Rep. of Germany ....... 3236388

[51] Int. Cl.$^4$ ............................................. C12Q 1/32
[52] U.S. Cl. ...................................... 435/25; 435/26; 435/810
[58] Field of Search .................................... 435/25, 26

[56] References Cited

U.S. PATENT DOCUMENTS 4,351,899  9/1982  Owen ..................................... 435/26
4,394,449  7/1983  Modrovich ........................... 435/26

FOREIGN PATENT DOCUMENTS 2818327  11/1978  Fed. Rep. of Germany .
37798    3/1979   Japan .
794071   1/1981   U.S.S.R. .

OTHER PUBLICATIONS

Chemical Abstracts I, 97:87841z, (1982).
Chemical Abstracts II, 99:118852b, (1983).
Chemical Abstracts III, 101:125929v, (1984).

*Primary Examiner*—Sidney Marantz
*Attorney, Agent, or Firm*—Felfe & Lynch

[57] ABSTRACT

Process for the selective production of the reduced oxygen species superoxide, hydrogen peroxide and hydroxyl radicals, wherein oxygen is reduced with NAD(P)H in the presence of an NAD(P)H-dependent, non-autoxidisable diaphorase, of an appropriate autoxidisable redox partner and optionally of an appropriate buffer system.

Also, process for the determination of superoxide dismutase in which a superoxide-yielding reaction is coupled with two competing superoxide-consuming reactions, one superoxide-consuming reaction being a conventional indicator reaction and the other superoxide-consuming reaction being the superoxide dismutase reaction, wherein, as superoxide-yielding reaction, there is used the reduction of oxygen with NAD(P)H in the presence of an NAD(P)H-dependent, non-autoxidisable diaphorase, of an autoxidisable one-electron step-inducing redox partner with a one-electron redox potential in the range of from $-150$ mV to $-500$ mV and optionally of an appropriate buffer system.

Also, process for the determination of NAD(P)H and of NAD(P)H-yielding reactions in which oxygen is reduced to hydrogen peroxide by NAD(P)H and the hydrogen peroxide is determined in knowm manner, wherein the reduction of the oxygen by NAD(P)H is carried out in the presence of an NAD(P)H-dependent, non-autoxidisable diaphorase, of an appropriate two-electron redox partner with a two-electron redox potential in the range of from 0 mV to 150 mV and of an appropriate buffer system.

Also, reagents for carrying out these processes.

29 Claims, 1 Drawing Figure

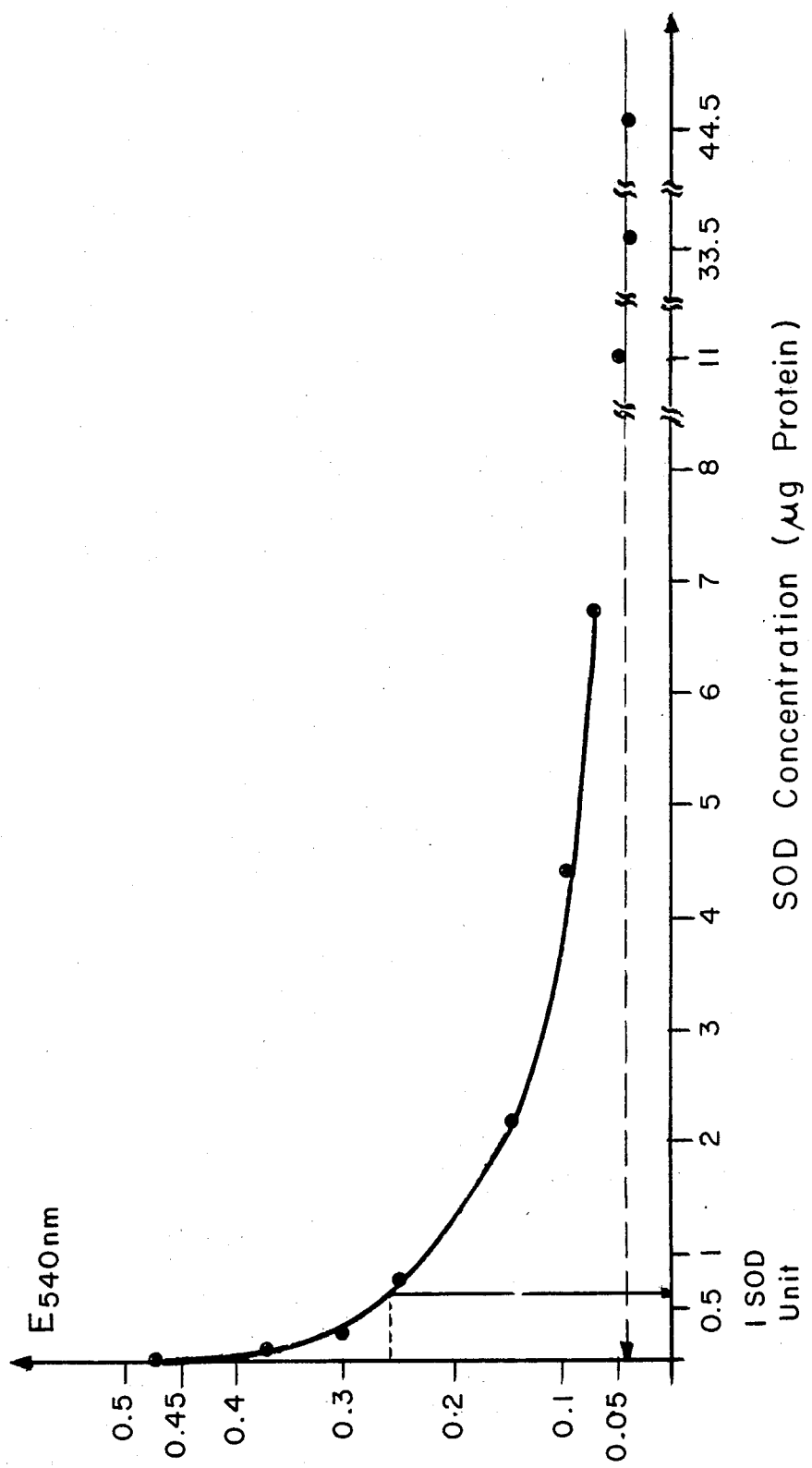

PROCESS FOR THE SELECTIVE PRODUCTION OF REDUCED OXYGEN SPECIES

The present invention is concerned with a process for the selective production of reduced oxygen species and with reagents suitable for this purpose.

In the case of the enzymatic reduction of the oxygen molecule, various products are formed, depending upon the number of transferring electrons, some of which products are very reactive. The following Table gives a survey of the possible redox reactions. Furthermore, examples are given of enzymes which are able to catalyse the redox reactions in question:

TABLE 1

| | Redox reactions of the oxygen molecule | | |
|---|---|---|---|
| No. | number of transferring electrons | product | enzyme example |
| 1 | 1E + 2E | $O_2{}^-$; $H_2O_2$ | xanthine oxidase |
| 2 | 2E | $H_2O_2$ | glucose oxidase |
| 3 | 3E | OH radical | non-specificity of xanthine oxidase |
| 4 | 4E | $H_2O$ | cytochrome oxidase |

Especially the superoxide ($O_2^-$) resulting in the case of a one-electron step has a considerable importance in the human and animal organism in the defense against foreign substances. Since the discovery in 1969 of the superoxide dismutases, i.e. enzymes which catalyse the dismutation of superoxide into hydrogen peroxide and oxygen, the field of oxygen biochemistry has achieved considerable scientific as well as economic interest. Questions as to which reduction products arise in the case of the most varied biochemical oxygen reductions, how these processes are influenced by the participating reaction components, which substrates are needed, which intermediate products arise and the like, thereby being in the foreground. Superoxide dismutase has already been used therapeutically, mainly against inflammations of the joints. A dependable method of determination is of economic importance for dosaging.

In the case of this question, the problem continually arises of analysing the most varied oxygen reduction products, as well as of determining the concentration of the enzymes and substrates participating in the reduction processes. For this purpose, there is a series of determination processes, especially for superoxide, hydrogen peroxide and the hydroxyl radical, as well as for the superoxide dismutases. A disadvantage of these processes of determination has hitherto been that the known enzymatic oxygen reduction processes always lead to a mixture of various reduction products, so that definitive statements regarding the physiological action of the reduction products, as well as the use of the reduction products for the analysis of enzymes reacting them and reaction components participating in their formation are decisively impaired. Thus, the superoxide-generating system, xanthine oxidase, mainly used today for the analysis of superoxide or superoxide dismutase, gives not only superoxide but also hydrogen peroxide (cf. Table 1. No. 1) and, in part, also the very reactive hydroxyl radical.

Therefore, it is an object of the present invention to provide a simple process with which it is possible selectively to produce in a one-, two- or three-electron step, superoxide, hydrogen peroxide or hydroxyl radicals. Surprisingly, this object can be achieved by reducing oxygen with NAD(P)H in the presence of an NAD(P)H-dependent, non-autoxidisable diaphorase and of a specially selected autoxidisable redox partner.

Thus, according to the present invention, there is provided a process for the selective production of the reduced oxygen species superoxide, hydrogen peroxide and hydroxyl radicals, wherein oxygen is reduced with NAD(P)H in the presence of an NAD(P)H-dependent, non-autoxidisable diaphorase and of an appropriate autoxidisable redox partner.

NAD(P)H-dependent, non-autoxidisable diaphorases are diaphorases which are not able to catalyse the reduction of oxygen by NAD(P)H.

Within the meaning of the present invention, all such diaphorases can, in principle, be used. Especially advantageously, there is used a diaphorase-active NADP-ferredoxin-(Cyt c)-oxidoreductase (E.C. 1.6.99.4), which can be obtained, for example, from spinach or *Euglena gracilis*. Commercially available diaphorase from *Clostridium kluyveri*, as well as a diaphorase from micro-organisms which is available from Boehringer Mannheim GmbH can also be used.

As autoxidisable redox partner, there can be used all substances which are able to transfer one or more electrons to oxygen. For the one-electron step, there can be used those redox partners, the one-electron redox potential $E'_o$ of which is in the range of from $-150$ mV to $-500$ mV. In particular, within the scope of the present invention there have proved to be useful bipyridilium salts, for example 1,1'-dimethyl-4,4'-bipyridilium chloride (paraquat) and 1,1'-dimethylene-2,2'-bipyridilium chloride (diquat): triazonium salts, for example 1-methyl-4-(4,6-dimethyl-2-sym-triazinyl)-pyridinium bromide and 1-methyl-4-(2-sym-triazinyl)-pyridinium bromide; anthraquinone derivatives, for example anthraquinone-2-sulphonic acid; nitrofuran derivatives, for example nitrofurantoin; ferredoxins; pteridines and isoalloxazines, for example riboflavine.

As redox partners for the two-electron step there can be used those substances, the two-electron redox potential $E'_o$ of which lies in the range of from 0 to 150 mV. As examples thereof, there are to be mentioned, in particular, quinone derivatives, especially p-benzoquinone derivatives, such as 2,5-dibromo-3-methyl-6-isopropyl-p-benzoquinone and 2,3-dimethyl-5,6-methylenedioxy-p-benzoquinone.

For the production of hydroxyl radicals, the end product of the three-electron step, the NAD(P)H-dependent non-autoxidisable diaphorase is coupled with those substances which, in the reduced state, can transfer an electron to hydrogen peroxide in air-saturated solution. Compounds which are especially preferred for this purpose include anthraquinone derivatives, such as anthraquinone-2-sulphonic acid; nitrofurantoin and ferredoxins.

The one- and two-electron reductions of oxygen are preferably carried out in air- or oxygen-saturated solution. The temperature can be varied within relatively wide limits, it being preferable to work at 18° to 25° C. or at ambient temperature. However, lower or higher temperatures can also be chosen, the upper temperature range being limited by the stability of the selected enzyme.

An appropriate buffer can possibly be added to the reagent mixture. Within the scope of the present invention, all buffers can be used which are effective in the pH range of from 6 to 9 and which are not radical receptors. A phosphate buffer of pH 7 to 8 has proved to be especially useful. The buffer is advantageously used in a concentration of 1 to 500 and preferably of 50 to 200 mmolar.

For the selective production of hydroxyl radicals, hydrogen peroxide is added under anaerobic conditions to the reaction solution of NAD(P)H-dependent, non-autoxidisable diaphorase, autoxidisable redox partner and optionally an appropriate buffer system in an appropriate solvent, preferably water. It is also possible to work under aerobic conditions and with the addition of superoxide dismutase. The primarily formed superoxide is thereby rapidly dismuted to oxygen and hydrogen peroxide, the latter then being selectively reduced to the hydroxyl radical in a further one-electron step.

The present invention also provides a reagent for carrying out the process according to the present invention which, possibly in separate units, contains in the form of a solution, of a powder mixture, of a reagent tablet or of a lyophilisate, NAD(P)H, an NAD(P)H-dependent, non-autoxidisable diaphorase and an autoxidisable redox partner, as well as optionally an appropriate buffer system.

Thus, according to the process of the present invention or with the help of the reagent according to the present invention, it is possible selectively to reduce the oxygen molecule to definite reduction products. Without having to fear disturbing side effects, the action of the individual oxygen reduction products on various substances, enzymatic systems or the like can, therefore, be observed. In this way, questions regarding the differential toxicity of the individual oxygen reduction products or the sensitivity of various biological materials towards the oxygen reduction products can be selectively investigated. For this purpose, the samples to be investigated are mixed with a test mixture which, besides NAD(P)H, contains an NAD(P)H-dependent, non-autoxidisable diaphorase and an autoxidisable redox partner for the production of superoxide, hydrogen peroxide or a hydroxyl radical, as well as optionally also an appropriate buffer system. The effect which is brought about by the oxygen reduction product produced can be analysed by the usual methods known to the expert.

In principle, in this way it is possible to measure the most varied reaction partners in such reactions in which the reduced oxygen species appears as a reaction partner or which are induced or catalysed by the reduced oxygen species. There is here mentioned, by way of example, the oxidation of hydroxylamine to nitrite ions by superoxide. Since this oxidation reaction proceeds stoichiometrically, the superoxide-providing system according to the present invention can be used for the determination of hydroxylamine. The nitrite ions formed by the oxidation of hydroxylamine are, for this purpose, determined by the conventional methods.

Various antibiotics, drugs, for example adriamycin, bleomycin and nitrofurantoin, and xenobiotics, for example herbicides and insecticides, are potential autoxidisable redox partners for a one-, two- or three-electron reduction of the oxygen according to the principle of the present invention. With the help of the process according to the present invention, it is possible to investigate the action of a particular drug or of a particular antibiotic on the oxygen reduction. For this purpose, a test system which contains NAD(P)H and an NAD(P)H-dependent, non-autoxidisable diaphorase and the substance to be investigated is brought into contact with oxygen. The resultant oxygen reduction product is determined by conventional processes. Thus, for example, with the help of hydroxylamine, it is possible to test whether superoxide has been formed. Nitrite ions possibly obtained by the oxidation of hydroxylamine can be measured by conventional methods.

For the detection of possibly formed hydrogen peroxide, there are available numerous known methods of determination. Trinder's reaction in its many known variants has proved to be especially suitable for this purpose.

The test solution can be investigated for possibly formed hydroxyl radicals with the help of methionine, the ethylene formed in the case of this known test being determined gas chromatographically. The possibility of selectively producing superoxide in a one-electron step with an NAD(P)H-dependent, non-autoxidisable diaphorase and an appropriate autoxidisable redox partner also leads to a selective detection of superoxide dismutase. Superoxide dismutase (SOD) catalyses the following reaction:

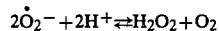

$$2\dot{O}_2^- + 2H^+ \rightleftharpoons H_2O_2 + O_2$$

Superoxide dismutase determinations generally depend upon the following principle: a superoxide-yielding reaction is coupled with two superoxide-consuming reactions, one of the superoxide-consuming reactions being an indicator reaction and the other superoxide-consuming reaction being a superoxide dismutase reaction. Consequently, the superoxide dismutase reaction competes with the indicator reaction for the superoxide molecules present. Consequently, the more superoxide dismutase is present in the test solution, the more is the indicator reaction inhibited. A survey of the at present most common superoxide dismutase determinations is given in the article "Superoxide dismutase assays: A review of methodology" from "Superoxide and superoxide dismutases" by A. M. Michelson, J. M. McCord and I. Fridovich, pub. Academic Press, New York, 1977.

As superoxide-yielding reaction, in the case of the at present most frequently used superoxide dismutase test, there is employed the xanthine oxidase reaction. As already mentioned, the xanthine oxidase reaction gives superoxide non-specifically but the side reactions also form hydrogen peroxide and the hydroxyl radical. The superoxide dismutase determination is thereby considerably disturbed. As indicator reaction there is usually used the cytochrome reduction test, the so-called adrenaline test or the nitro blue tetrazolium test. These multi-component systems also give rise to considerable difficulties if various reduced oxygen species occur simultaneously. Furthermore, in the case of multi-component systems, there is to be reckoned with an undesired but always measurable additional catalysis by non-specific bound transition metal ions, for example iron and copper.

If superoxide produced in the manner according to the present invention is used for the determination of superoxide dismutase, then a disturbance-free test is obtained. As indicator reaction, any known indicator reaction can be coupled. For the determination of superoxide dismutase, there has proved to be especially useful the combination of the superoxide-yielding reaction according to the present invention with the hydroxylamine test, hydroxylamine hereby being oxidised to nitrite ions by the resultant superoxide which, after diazotisation and subsequent azo coupling, can be measured photometrically.

The present invention also provides a process for the determination of superoxide dismutase by coupling of a superoxide-yielding reaction with a superoxide-consuming indicator reaction which competes with the dismutation of the superoxide catalysed by the superoxide dismutase, whereby, as superoxide-yielding reaction, there is used the reduction of oxygen by NAD(P)H in the presence of an NAD(P)H-dependent, non-autoxidisable diaphorase and of an appropriate autoxidisable one-electron redox partner, as well as optionally of an appropriate buffer system.

Furthermore, the present invention provides a reagent for the determination of superoxide dismutase which, in the form of a solution, of a powder mixture, of a reagent tablet or of a lyophilisate, contains NAD(P)H, an NAD(P)H-dependent, non-autoxidisable diaphorase, an autoxidisable one-electron redox partner and the components for an appropriate indicator reaction, as well as optionally an appropriate buffer system.

As NAD(P)H-dependent, non-autoxidisable diaphorases, there are especially preferred those enzymes mentioned hereinbefore. As autoxidisable one-electron redox partners, there are also preferred those substances mentioned hereinbefore. As indicator reaction, there is preferably used the oxidation of hydroxylamine to nitrite ions, with the subsequent determination of the nitrite ions. As components of this reaction, to the above-mentioned reagent there is then added hydroxylamine and the substances necessary for the determination of the nitrite ions, for example sulphanilic acid and α-naphthylamine or sulphanilamide and naphthylethylenediamine.

The various components are preferably contained in the reagent in such amount ratios that, in 2 ml. of final test solution, the following concentration ratios are present:

1–10 μmole NAD(P)H
0.05–0.5 mg. diaphorase
0.1–5 μmole redox partner
1–10 μmole indicator substance
50–200 μmole buffer, pH 6–9

Especially preferred is a test mixture which, in 2 ml. of water, contains:

5 μmole NAD(P)H
0.5 mg. diaphorase
1 μmole redox partner
1 μmole hydroxylamine and
60–100 μmole phosphate buffer, pH 7.5–8.0.

The selective reduction of the oxygen with NAD(P)H in a two-electron step to hydrogen peroxide in the presence of an NAD(P)H-dependent, non-autoxidisable diaphorase and of an appropriate two-electron redox partner, as well as optionally of an appropriate buffer system also makes possible a determination of NAD(P)H which is easy to carry out. For this purpose, the sample to be investigated is saturated with oxygen and mixed with a test mixture which contains an NAD(P)H-dependent, non-autoxidisable diaphorase, an appropriate two-electron redox partner and optionally an appropriate buffer system, as well as a hydrogen peroxide detection system. The hydrogen peroxide concentration measured with the help of the hydrogen peroxide detection system is a direct measure of the NAD(P)H present in the sample.

The following Examples are given for the purpose of illustrating the present invention:

EXAMPLE 1

Production and determination of superoxide 2 ml. Phosphate buffer (0.2M; pH 7.8) are placed into a 10 ml. reagent vessel. Air is passed through the buffer solution for 30 minutes at ambient temperature in order to saturate it with air. Thereafter, the mixture is mixed with 0.1 ml. of an aqueous solution which contains 1 μmole NADH, as well as with 0.1 ml. of an aqueous solution which contains 0.4 μmole anthraquinone-2-sulphonic acid. The solution thus obtained is mixed with 0.5 mg. diaphorase (Boehringer Mannheim GmbH, obtained from microorganisms; lyophilised) dissolved in 1 ml. distilled water. The resultant superoxide is detected with the help of the known hydroxylamine reaction.

For this purpose, to the reaction mixture there is additionally added to the already mentioned substances 0.1 ml. of a hydroxylammonium chloride solution, prepared by dissolving 6.9 mg. hydroxylammonium chloride in 10 ml. distilled water. The resultant nitrite ions are determined by the addition of a 1% (w/v) sulphanilamide solution in 25% hydrochloric acid and after the addition of 0.02% aqueous naphthylethylenediamine dihydrochloride, as well as by measurement of the azo coloured material formed at 540 nm.

From the measured extinction values, there can be determined the yield of superoxide by comparison with a calibration curve obtained with known nitrite concentrations.

Similar results are achieved when, instead of the above-mentioned anthraquinone-2-sulphonic acid, there are used other one-electron receptors, for example 1,1′-dimethyl-4,4′-bipyridilium chloride, 1-methyl-4-(4,6-dimethyl-2-sym-triazinyl)-pyridinium bromide, 1-methyl-4-(2-sym-triazinyl)-pyridinium bromide or nitrofurantoin.

EXAMPLE 2

Production of hydrogen peroxide 2 ml. Air-saturated phosphate buffer (0.2M, pH 7.8) are prepared in a 10 ml. reagent vessel in the manner described in Example 1. To this are added 0.1 ml. of an aqueous solution which contains 1 μmole NADH and 0.1 ml. of an aqueous solution which contains 0.4 μmole 2,5-dibromo-3-methyl-6-isopropyl-p-benzoquinone.

The so obtained solution is mixed with 0.5 mg. diaphorase (Boehringer Mannheim GmbH; obtained from micro-organisms; lyophilised), dissolved in 1 ml. of distilled water. The hydrogen peroxide formed is determined according to known methods, for example by Trinder's method.

Comparable results are obtained when, instead of the above-mentioned redox partner, there are used other two-electron redox partners, for example 2,3-dimethyl-5,6-methylenedioxy-p-benzoquinone.

EXAMPLE 3

Production and determination of hydroxyl radicals (A) 2 ml. of phosphate buffer (0.2M, pH 7.8) are placed into a 10 ml. reagent glass. There are successively added thereto, under anaerobic conditions, 0.1 ml. of an aqueous solution which contains 0.1 μmole NADH; 0.1 ml. of an aqueous solution which contains 0.4 μmole anthraquinone-2-sulphonic acid; 0.1 ml. of a 2% hydrogen peroxide solution; and 0.5 mg.

diaphorase (Boehringer Mannheim GmbH; obtained from micro-organisms; lyophilised), dissolved in 1 ml. distilled water.

The resultant hydroxyl radicals are detected in known manner with the help of methionine splitting. From the methionine, ethylene is split off, which can be measured gas chromatographically.

(B) 2 ml. of phosphate buffer (0.2M; pH 7.8), which has been saturated with air in the manner described in Example 1, are placed in a 10 ml. reagent glass. There are also added 0.1 ml. of an aqueous solution which contains 0.1 μmole NADH; 0.1 ml. of an aqueous solution which contains 0.4 μmole N-(5-nitro-2-furylidene)-1-aminohydantoin(nitrofurantoin); 200 Units (as defined in Example 4) of superoxide dismutase; and 1 mg. NADP-ferredoxin-(Cyt-c)-oxidoreductase, dissolved in 1 ml. distilled water.

The hydroxyl radicals formed are, as described above, determined by the addition of methionine.

EXAMPLE 4

Determination of superoxide dismutase

1. Preparation of a calibration curve

Into a 10 ml. test tube is placed 0.5 ml. water and the following solutions are pipetted into it: 1.0 ml. air-saturated phosphate buffer (pH 7.8) (65 μmole), 0.1 ml. hydroxylamine hydrochloride (1.0 μmole); 0.1 ml. anthraquinone-2-sulphonic acid (1.0 μmole); and 1 ml. diaphorase (0.5 mg. protein).

The solution mixture is vigorously shaken and thereafter mixed with 0.1 ml. superoxide dismutase (increasing concentrations of 0 to 100 Units) and 0.1 ml. NADH (5 μmole).

The solution obtained is vigorously mixed and incubated for 15 minutes at 22° C. After this reaction time, 0.5 ml. of this reaction solution is mixed with nitrite reagent which consists of 0.5 ml. of a 1% (w/v) sulphanilamide solution in 25% hydrochloric acid and 0.5 ml. of a 0.02% (w/v) naphthylethylenediamine dichloride solution in water. The extinction is followed spectrophotometrically at 540 nm. FIG. 1 of the accompanying drawing shows the calibration curve thus produced.

For superoxide dismutase, one enzyme unit is given as the amount of enzyme which brings about a 50% inhibition of the detector reaction, i.e. in the present case the oxidation of hydroxylamine to nitrite ions.

From FIG. 1, there is given for the investigated enzyme an activity of one unit per 0.7 μg. protein according to the following equation:

$$E_{\frac{1}{2}} = \frac{E^{540}_{max} + E^{540}_{end\ value}}{2} = \frac{0.475 + 0.04}{2} = 0.26 = 1\ SOD\ unit$$

2. Determination of unknown superoxide dismutase concentrations

In the same manner as described above, there can also be determined unknown superoxide dismutase concentrations in that, instead of the standard with known superoxide dismutase concentration, there is used the corresponding amount of a sample with unknown superoxide dismutase concentration, the measured extinction values being compared with the calibration curve, there thus being determined the superoxide dismutase concentration corresponding to the measured extinction value.

EXAMPLE 5

Determination of NADH

Hydrogen peroxide is produced in the manner described in Example 2. Instead of the solution with a known NADH content, there is merely employed the sample solution with an unknown NADH content. The amount of hydrogen peroxide formed is, after the reaction with hydrogen peroxide formation from NADH has taken place with complete utilisation of the NADH, measured as follows:

The following solutions are prepared:

Solution 1: 100 mg. dichlorophenolsulphonic acid are dissolved in 4 ml. ethanol and diluted with 4 ml. water.

Solution 2: 0.1 g. 4-aminoantipyrine are dissolved in 2.5 ml. water.

Solution 3: 10 mg. peroxidase are dissolved in 10 ml. water.

For the determination of the hydrogen peroxide, to 1 ml. of the hydrogen peroxide-containing solution to be tested are added 0.8 ml. phosphate buffer (0.1M; pH 7.0), 0.4 ml. of Solution 1, 0.1 ml. of Solution 2 and, for initiating the reaction, 0.1 ml. of Solution 3. After a reaction time of 30 minutes, the extinction is measured at 540 nm. By comparison of the found extinction value with an appropriate calibration curve, the NADH content of the investigated sample is determined.

The calibration curve is obtained by carrying out the above determination process with samples which have different but known NADH concentrations.

It will be understood that the specification and examples are illustrative but not limitative of the present invention and that other embodiments within the spirit and scope of the invention will suggest themselves to those skilled in the art.

What is claimed is:

1. A process for the selective production of the reduced oxygen species superoxide, hydrogen peroxide or hydroxyl radicals, comprising reducing oxygen with NAD(P)H in the presence of an NAD(P)H-dependent, non-autoxidizable diaphorase and an autoxidizable redox partner.

2. The process of claim 1, wherein the NAD(P)H-dependent, non-autoxidizable diaphorase is NADP-ferredoxin-(Cyt c)-oxidoreductase or diaphorase from microorganisms.

3. The process of claim 1 to produce superoxide, wherein the autoxidizable redox partner is a one-electron step-inducing substance with a one-electron redox potential $E'_o$ in the range of from $-150$ mV to $-500$ mV.

4. The process of claim 2 to produce superoxide wherein the autoxidizable redox partner is a bipyridilium salt, a triazonium salt, an anthraquinone derivative, a nitrofuran derivative, a ferredoxin, a pteridine or an isoalloxazine.

5. The process of claim 1 for the production of hydrogen peroxide wherein the autoxidizable redox partner is a two-electron step-inducing substance with a two-electron redox potential $E'_o$ in the range of from 0 mV to 150 mV.

6. The process of claim 2 to produce hydrogen peroxide, wherein the autoxidizable redox partner is a quinone derivative.

7. The process of claim 1 to produce hydroxyl radicals, wherein the autoxidizable redox partner is a one-electron step-inducing substance with a one-electron redox potential $E_o'$ in the range of from $-150$ mV to $-500$ mV in the presence of superoxide dismutase.

8. A process for the selective production of hydroxyl radicals comprising reducing hydrogen peroxide with NAD(P)H, under anaerobic conditions in the presence of NAD(P)H-dependent, non-autoxidizable diaphorase and an autoxidizable, one-electron step-inducing redox partner with a one-electron redox potential $E_o$ in the range of from $-150$ mV to $-500$ mV.

9. The process of claim 1 wherein the reaction is buffered to the range of pH 6–9.

10. A reagent for the production of the reduced oxygen species superoxide, hydrogen peroxide or hydroxyl radicals by the reduction of oxygen or hydrogen peroxide with NAD(P)H, comprising NAD(P)H, an NAD(P)H-dependent, non-autoxidizable diaphorase and autoxidizable redox partner.

11. The reagent of claim 10 wherein the NAD(P)H-dependent, non-autoxidizable diaphorase is NADP-ferredoxin-Cyt c)-oxidoreductase or diaphorase from microorganisms.

12. The reagent of claim 10 for the production of superoxide wherein the autoxidizable redox partner is a substance which is able to induce a one-electron step and has a one-electron redox potential $E_o'$ in the range of $-150$ mV to $-500$ mV.

13. The reagent of claim 11 for the production of superoxide wherein the redox partner is a bipyridilium salt, a triazonium salt, an anthraquinone derivative, a nitrofuran derivative, a ferredoxin, a pteridine or an isoalloxazine.

14. The reagent of claim 10 for the production of hydrogen peroxide wherein the autoxidizable redox partner is a substance which is able to induce a two-electron step and has a two-electron redox potential $E_o'$ in the range of from 0 to mV to 150 mV.

15. The reagent of claim 11 for the production of hydrogen peroxide wherein the redox partner is a quinone derivative.

16. The reagent of claim 10 for the production of hydroxyl radicals wherein the autoxidizable redox partner is a substance which is able to induce a one-electron step and has a one-electron redox potential $E'$ in the range of from $-150$ mV to $-500$ mV and additionally contains superoxide dismutase.

17. A method for the determination of superoxide dismutase comprising the steps of coupling a superoxide-yielding reaction with two competing superoxide-consuming reactions, one superoxide-consuming reaction being an indicator reaction and the other superoxide-consuming reaction being a superoxide dismutase reaction, wherein, as superoxide-yielding reaction, there is used the reduction of oxygen with NAD(P)H in the presence of an NAD(P)H-dependent, non-autoxidizable diaphorase, of an autoxidizable one-electron step-inducing redox partner with a one-electron redox potential in the range of from $-150$ mV to $-500$ mV.

18. The method of claim 17 wherein the NAD(P)H-dependent, non-autoxidizable diaphorase is NADP-ferredoxin-(Cyt c)-oxidoreductase or diaphorase from microorganisms.

19. The method of claim 17 wherein the redox partner is a bipyridilium salt, a triazonium salt, an anthraquinone derivative, a nitrofuran derivative, a ferredoxin, a pteridine or an isoalloxazine.

20. A reagent for the determination of superoxide dismutase by the process of claim 17 comprising NAD(P)H, an NAD(P)H-dependent, non-autoxidizable diaphorase, an autoxidizable, one-electron step-inducing redox partner with a one-electron redox potential in the range of from $-150$ mV to $-500$ mV and the components for an indicator reaction.

21. Reagent of claim 20 wherein the NAD(P)H-dependent, non-autoxidizable diaphorase is NADP-ferredoxin (Cyt c)-oxidoreductase or diaphorase from microorganisms.

22. The reagent of claim 20 wherein the redox partner is a bipyridilium salt, a triazonium salt, an anthraquinone derivative, a nitrofuran derivative, a ferredoxin, a pteridine or an isoalloxazine.

23. The reagent of claim 20 wherein the components for the indicator reaction are a hydroxylammonium salt and a test system for the detection of nitrite ions.

24. A method for the determination of NAD(P)H and NAD(P)H-yielding reactions comprising reducing oxygen to hydrogen peroxide by NAD(P)H and determining the hydrogen peroxide, wherein the reduction of the oxygen by NAD(P)H is carried out in the presence of an NAD(P)H-dependent, non-autoxidizable diaphorase, of a two-electron redox partner with a two-electron redox potential in the range of from 0 mV to 150 mV and of a buffer system.

25. The method of claim 24 wherein the NAD(P)H-dependent, non-autoxidizable diaphorase, is NADP-ferredoxin-(Cyt c)-oxidoreductase or diaphorase from microorganisms.

26. The method of claim 24 wherein a quinone derivative is used as redox partner.

27. A reagent for the determination of NAD(P)H and of NAD(P)H-yielding reactions according to the method of claim 24 comprising, in the form of a solution, of a powder mixture, a reagent tablet or a lyophilisate: an NAD(P)H-dependent, non-autoxidizable diaphorase, and two-electron redox partner with a two-electron redox potential in the range of from 0 mV to 150 mV, and a hydrogen peroxide detection system.

28. The process of claim 1, wherein the NAD(P)H-dependent, non-autoxidizable diaphorase is diaphorase from *Clostridium kluyveri*.

29. The reagent of claim 10 wherein the NAD(P)H-dependent, non-autoxidizable diaphorase is diaphorase from *Clostridium kluyveri*.

* * * * *